United States Patent [19]

Lundberg

[11] Patent Number: 6,066,108
[45] Date of Patent: May 23, 2000

[54] METHOD AND APPARATUS FOR TREATING AND PREVENTING SACROILIAC JOINT INJURIES

[76] Inventor: Leslie C. Lundberg, 303 Dublin Cir., Smithville, Mo. 64080

[21] Appl. No.: 09/093,587

[22] Filed: Jun. 8, 1998

[51] Int. Cl.[7] .................................................. A61F 5/00
[52] U.S. Cl. .................................. 602/23; 602/19; 2/919
[58] Field of Search ................................. 602/5, 19, 20, 602/23; 128/869, 873, 875, 876; 2/44, 311, 313, 92, 919

[56] References Cited

U.S. PATENT DOCUMENTS

| | | |
|---|---|---|
| 1,008,500 | 11/1911 | Thornton . |
| 1,316,915 | 9/1919 | Meyer et al. . |
| 1,678,584 | 7/1928 | Branson . |
| 1,722,192 | 7/1929 | Brokaw .......................................... 2/44 |
| 1,812,529 | 6/1931 | Haulbrook et al. . |
| 3,717,143 | 2/1973 | Johnson . |
| 4,709,692 | 12/1987 | Kirschenberg et al. . |
| 4,836,194 | 6/1989 | Sebastian et al. . |
| 4,926,502 | 5/1990 | Miyamura . |
| 4,926,845 | 5/1990 | Harris . |
| 4,993,409 | 2/1991 | Grim . |
| 5,038,760 | 8/1991 | Osborn . |
| 5,062,414 | 11/1991 | Grim . |
| 5,205,815 | 4/1993 | Saunders . |
| 5,256,135 | 10/1993 | Avihod . |
| 5,334,134 | 8/1994 | Saunders . |
| 5,499,965 | 3/1996 | Sanchez .................................... 602/19 |
| 5,503,620 | 4/1996 | Danzger .................................... 602/19 |
| 5,709,648 | 1/1998 | Webb ....................................... 602/19 |

*Primary Examiner*—Richard J. Apley
*Assistant Examiner*—Denise Pothier
*Attorney, Agent, or Firm*—Hovey, Williams, Timmons & Collins

[57] ABSTRACT

A system for preventing and treating most lower back disorders provides an upwardly and forwardly directed compressive force exerted against the sacroiliac joint of the human body. Particularly, an inventive back brace is disclosed as including a support dimensioned to extend along the backside of the body generally from the lumbar region of the spine downwardly at least to the ischial tuberosity of each of the pelvic bones. A pair of adjustable leg straps and a flexible wrap dimensioned to extend around the lower torso are operatively connected to the support for tightening the support against the buttocks of the wearer so as to provide the desired compressive force against the sacroiliac joint.

36 Claims, 4 Drawing Sheets

METHOD AND APPARATUS FOR TREATING AND PREVENTING SACROILIAC JOINT INJURIES

BACKGROUND OF THE INVENTION

1. Field of the Invention

The present invention relates generally to medical devices and, more particularly, to a method and apparatus for treating and preventing most lower back injuries.

2. Discussion of Prior Art

It has been determined that a majority of lower back disorders and lower back pain involve an injury to the sacroiliac joint. Furthermore, injury to the sacroiliac joint is typically caused by over-twisting or excessive anterior or posterior tilt of the pelvis, causing injury to the sacroiliac ligaments connecting the lumbosacral region of the spine to the pelvic bones.

In the past, virtually all conventional lower back supports have attempted to prevent and treat injuries to the lower back by providing a compression wrap around the lower torso of the wearer. However, conventional back supports typically do not extend much below the waistline of the wearer. It will be appreciated by those of ordinary skill in art that a significant portion of the sacroiliac joint is located well below the waistline of the body. It may, in fact, be said that the sacroiliac joint is generally located under the gluteal muscle in the buttocks region of the body. It is believed that proper treatment and support for the sacroiliac joint requires that pressure be applied in a generally forward and upward direction against the joint. Accordingly, most known conventional back supports simply do not support most, if not all, of the sacroiliac joint. Although a compression wrap about the lower torso will provide support for the injured tissues above the waistline, most lower back disorders occur at the base of the spine (i.e., at the sacroiliac joint), and consequently traditional supports are ineffective in most applications.

There have been numerous back supports with structure disposed below the waistline for anchoring the compression wrap about the lower torso so as to prevent upward migration of the wrap during use. However, the anchor structure is not designed or configured to provide the compressive pressure necessary for properly treating and supporting the sacroiliac joint. As indicated above, preventing upward migration of the compressive wrap may be helpful when treating the relatively uncommon injuries to tissue above the sacroiliac joint, however, this design is still ineffective in treating and preventing most lower back disorders.

It is also important to note that a number of traditional lower back supports tend to have complex, uncomfortable, and expensive constructions. In addition, proper positioning of traditional lower back supports on the body is often difficult. This is especially true with conventional supports having anchoring structure for preventing upward migration of the compressive wrap.

OBJECTS AND SUMMARY OF THE INVENTION

Responsive to these and other problems, an important object of the present invention is to provide a system that is effective in treating and/or preventing most lower back disorders and lower back pain. In this respect, it is an important object of the present invention to provide a back brace that is particularly designed to effectively support the sacroiliac joint. Another important object of the present invention is to provide a back brace that applies an upwardly and forwardly directed force against the sacroiliac joint. Along these lines, it is also an important object of the present invention is to provide such a brace that permits user adjustment of the compressive force applied against the sacroiliac joint. Yet another important object of the present invention is to provide a back brace having a sacroiliac joint support that generally overlies the buttocks of the wearer. An additional object of the present invention is to provide a comfortable lower back brace that has an inexpensive and simple construction and that is easily positioned on the wearer.

In accordance with these and other objects evident from the following description of the preferred embodiment, the present invention contemplates a back brace including a support dimensioned to overlie the sacroiliac joint along the backside of the user. The support may consequently be caused to apply a compressive force against the sacroiliac joint that provides the proper support for the joint. It is particularly noted that the back brace includes structure for causing the support to exert an adjustable force against the sacroiliac joint in a generally upward and forward direction. The inventive support may comprise a flexible element dimensioned to extend from the lumbar region of the spine downwardly at least to the ischial tuberosity of each of the pelvic bones of the user. On the other hand, conventional compressive wraps extending only slightly below the waistline are simply not capable of providing the necessary upwardly and forwardly directed compressive force for proper support of the sacroiliac joint.

The preferred structure for causing the support to exert the desired compressive force against the sacroiliac joint comprises at least one element operatively connected to the support and dimensioned to wrap around the body for adjustably tightening the support against the body. In this respect, the back brace may include a flexible wrap dimensioned to extend around the lower torso. It may be said that the sacroiliac joint support projects from the flexible wrap to generally overlie the buttocks and extend downwardly to the crotch of the wearer when the brace is worn. The back brace may also include a pair of adjustable leg straps operatively connected to the support and configured to extend around the respective leg of the wearer for adjustably tightening the support against the body. Furthermore, the back brace may be provided with a flexible tightening cuff attached to the wrap and dimensioned to wrap around the lower torso of the user, with the ends of the cuff having adjustable attachment structure for adjustably attaching the ends to one another.

Other aspects and advantages of the present invention will be apparent from the following detailed description of the preferred embodiments and the accompanying drawing figures.

BRIEF DESCRIPTION OF THE DRAWING FIGURES

A preferred embodiment of the invention is described in detail below with reference to the attached drawing figures, wherein.

DETAILED DESCRIPTION OF THE PREFERRED EMBODIMENT

Figure 2:
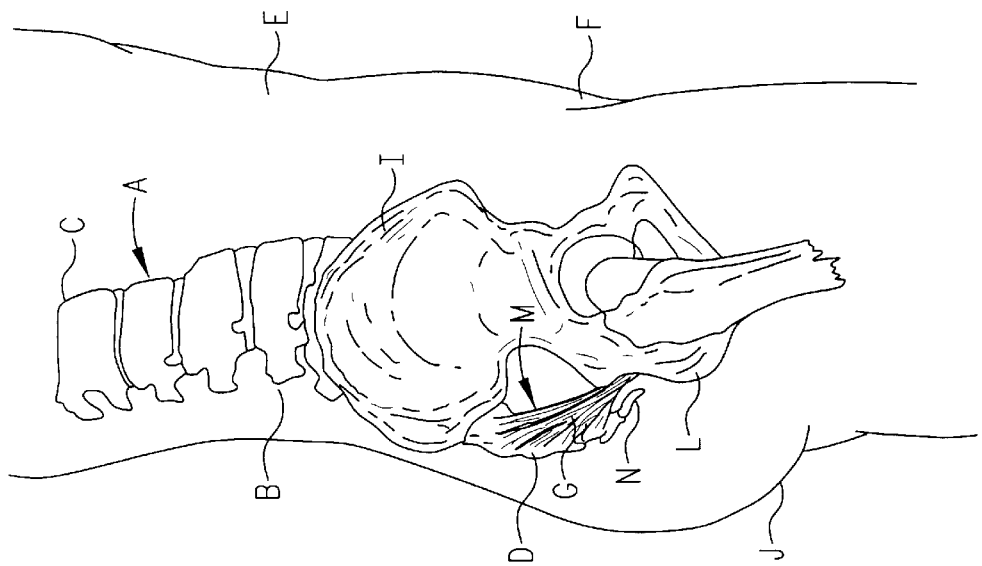
FIG. 2 is a diagrammatic rear elevational view of the lower torso, upper legs and pelvic region of the human body, particularly illustrating the sacroiliac joint including the ligaments extending between the lumbosacral region of the spine and the pelvic bones.
Figure 1:
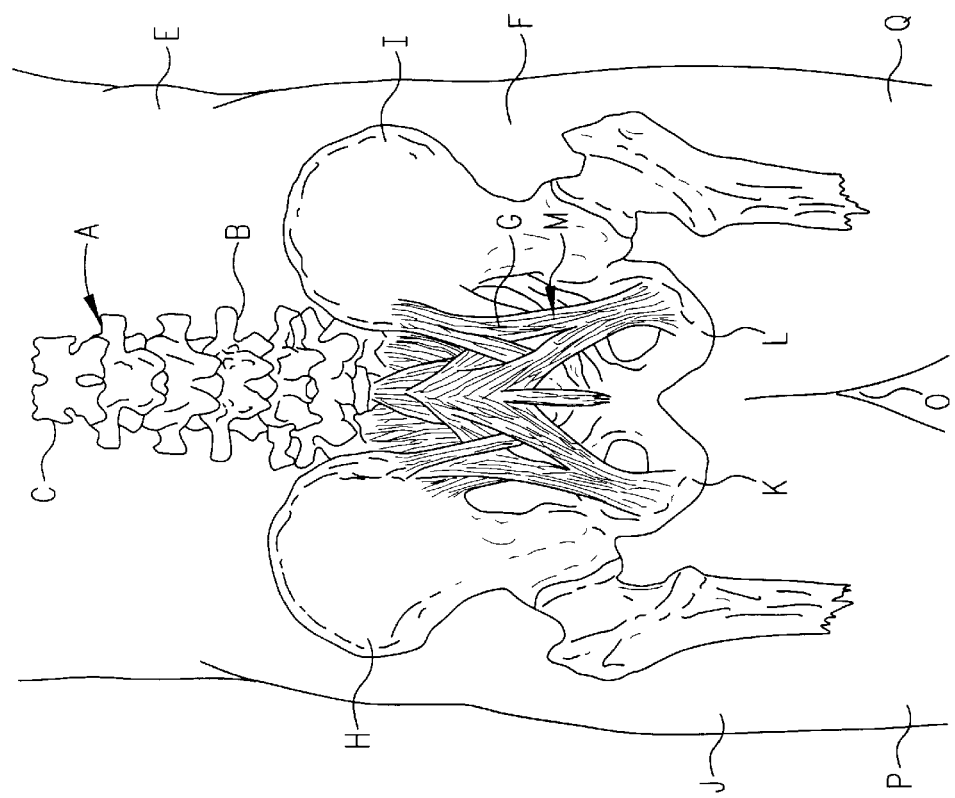
FIG. 1 is a diagrammatic right side elevational view of the lower torso, upper legs and pelvic region of the human body, particularly illustrating the sacroiliac joint including the ligaments extending between the lumbosacral region of the spine and the pelvic bones.
Figure 5:
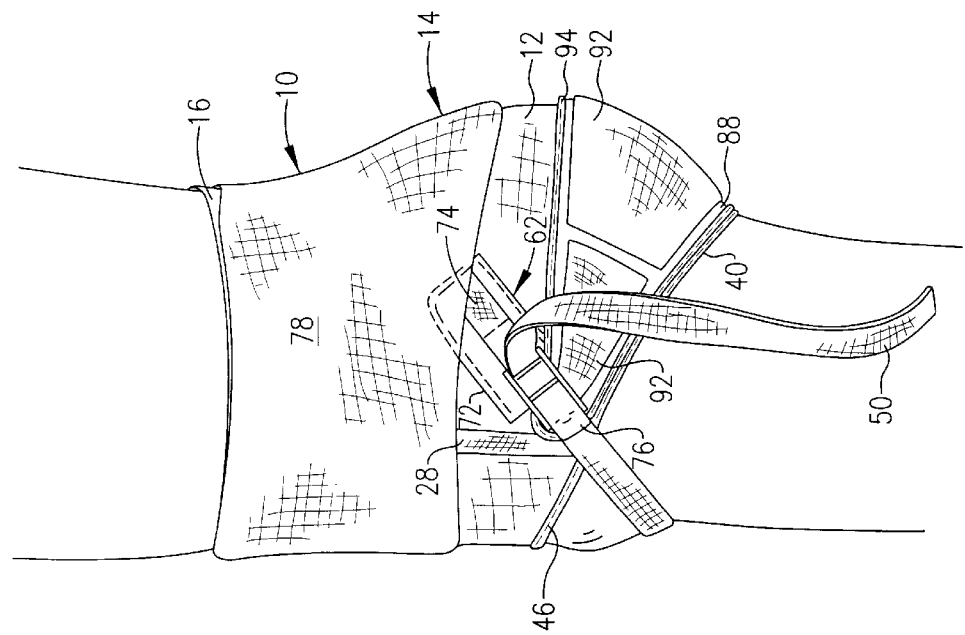
FIG. 5 is a left side elevational view of the back brace, particularly illustrating the support extending downwardly below the location of the ischial tuberosity of the left pelvic bone.
Figure 3:
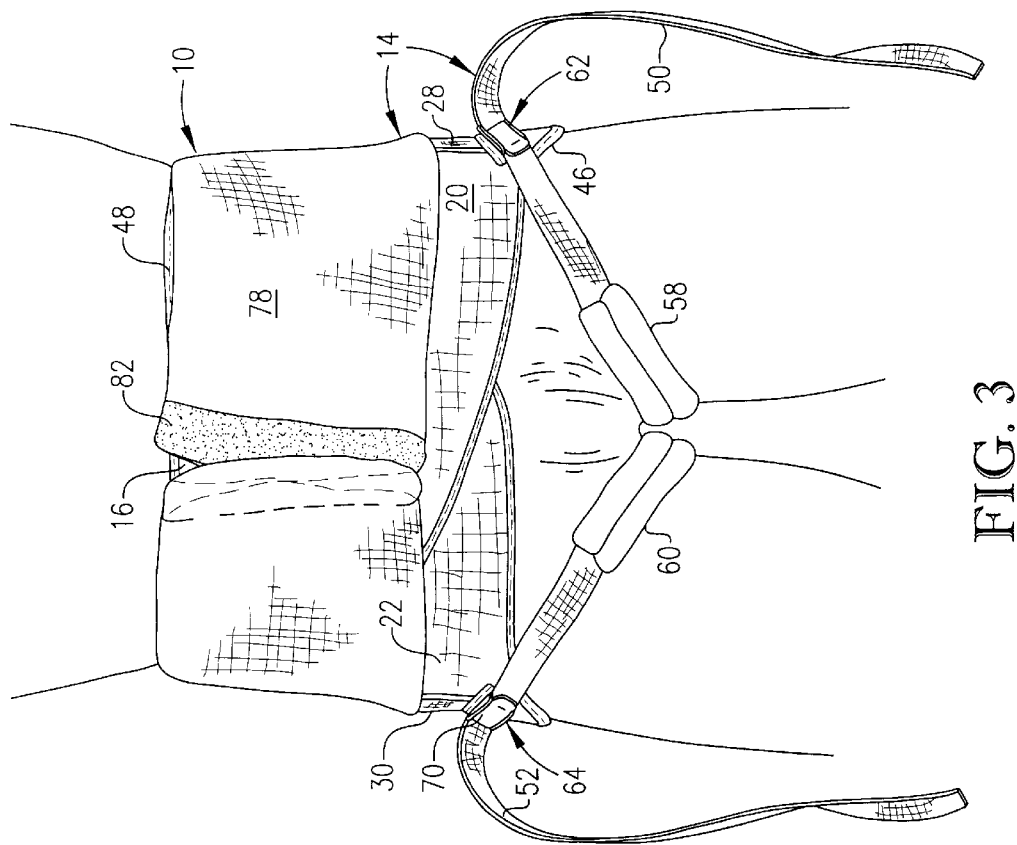
FIG. 3 is a front elevational view of a back brace constructed in accordance with the principles of the present invention and positioned on the lower torso and pelvic region of a wearer, particularly illustrating the leg straps, flexible wrap and tightening cuff secured to the body for tightening the support against the sacroiliac joint.
Figure 4:
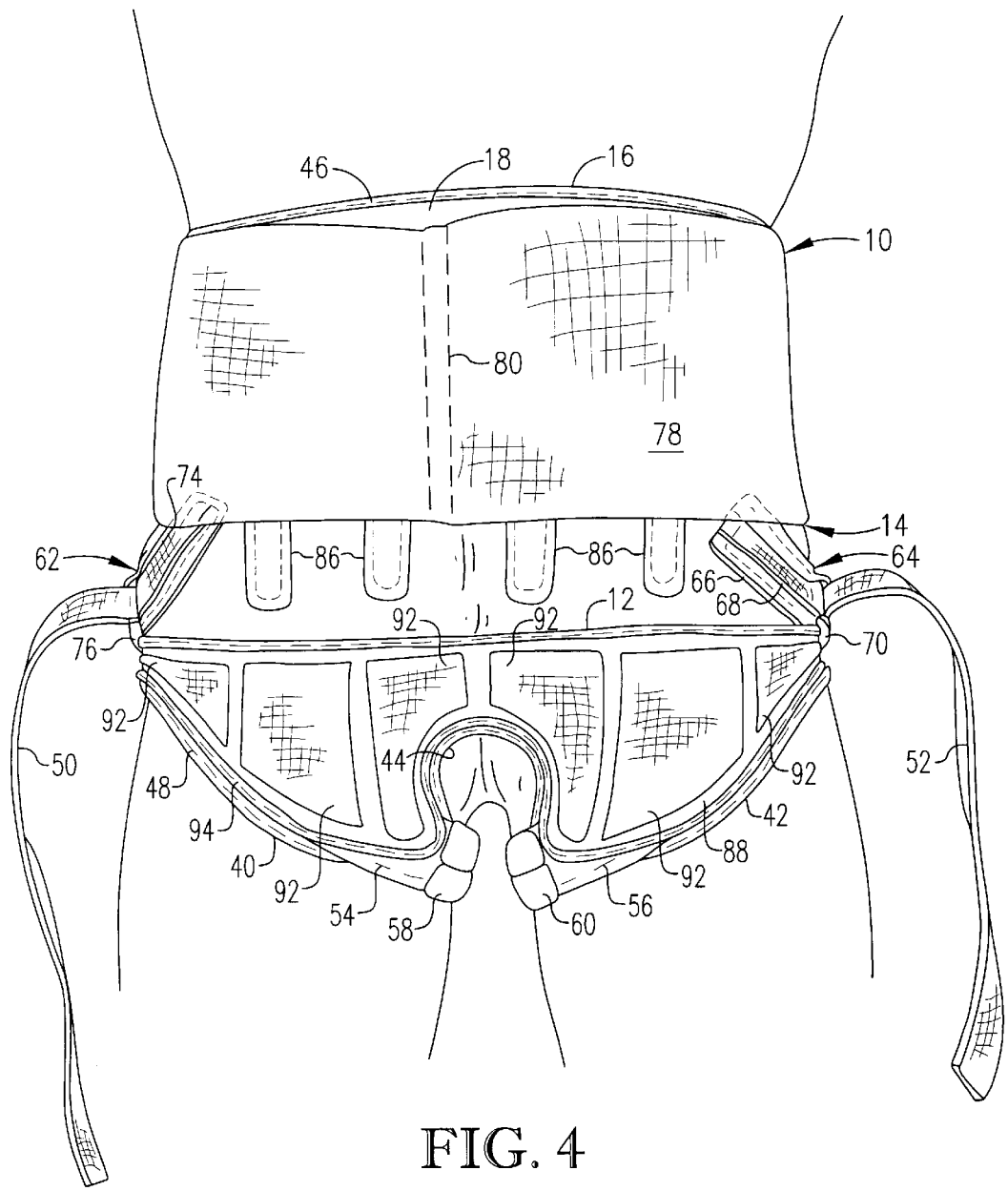
FIG. 4 is a rear elevational view of the back brace, particularly illustrating the support overlying the buttocks and extending downwardly to the crotch of the wearer.

Turning initially to FIG. 1, the spinal column A includes a lumbar region B comprising five interconnected vertebra disposed between the thoracic region C of the spine and the sacrum D. Generally speaking, the lumbar vertebra B and the sacrum D (collectively the lumbosacral region of the spine) extend from the lower torso E downwardly into the pelvis or groin region F of the body. A plurality of ligaments, generally referenced by the letter G, serve to connect the lumbosacral region B,D of the spine to the pelvic bones H and I (see also FIG. 2). It will be appreciated that these ligaments include the sacrotuberous ligament, the long and short posterior sacroiliac ligaments, the dorsal cacrococcgeal ligament, etc. Further, these ligaments are generally disposed beneath the gluteal muscle defining the buttocks J. It will also be noted that none of the ligaments extend below the ischial tuberosity K and L of the pelvic bones H and I, respectively.

The lumbosacral region B,D of the spine A, the pelvic bones H,I and the ligaments G cooperatively define the sacroiliac joint M along the backside of the body. Similar to the other joints of the human body, the ligaments G allow relative movement between the spine A and the pelvic bones H,I, although such movement of the sacroiliac joint M is very limited. Generally speaking, movement of the sacroiliac joint M is limited to anterior tilt of the pelvis (i.e., forward pelvic thrust), posterior tilt of the pelvis (i.e., rearward pelvic thrust), and very minimal twisting about the longitudinal axis of the spine A.

As those ordinarily skilled in the art will appreciate, most injuries to the lower back consequently involve overtwisting of the spine A relative to the pelvic bones H,I or excessive anterior or posterior tilt of the pelvis, causing injury to the ligaments G. Treatment and prevention of such injuries require bracing, or support of the sacroiliac joint M, as is commonly prescribed with injuries to the other joints of the body. In particular, treatment and prevention of the sacroiliac joint injuries require immobilization of the joint M or, at the very least, restriction against untoward movement of the joint M. A forwardly and upwardly directed compressive force exerted against the sacroiliac joint M is also helpful because it provides support for the joint and, more particularly, urges the pelvis to tilt anteriorly, which relieves strain on the ligaments G (i.e., anterior tilt of the pelvis corresponds with slight contraction of the ligaments G).

However, traditional back braces (not shown) simply are not capable of providing such support for the sacroiliac joint M. Most conventional back braces comprise compressive wraps dimensioned to fit around the lower torso E and to extend from the lumbar spine region B to a point spaced only slightly below the waist. Moreover, all known prior art braces terminate short of the coccyx N (see FIG. 1). Accordingly, conventional braces provide only a forwardly directed force against the uppermost portion of the sacroiliac joint M. However, it is believed that the best method for providing the support necessary to treat and prevent injury to the sacroiliac joint M involves application of a forwardly and upwardly directed force against substantially the entire joint M, as previously indicated. Thus, a forwardly directed force exerted against only the uppermost portion of the sacroiliac joint M is deficient in treating and preventing most lower back disorders. It will be noted that a number of conventional braces include structure extending below the coccyx N, such as a strap for wrapping under the crotch O (see FIG. 2) or around one of the legs P or Q, although such structure is designed only to anchor the wrap against upward migration along the body not to brace the sacroiliac joint M.

Turning now to FIGS. 3–7, the present invention concerns a back brace 10 that is especially designed to provide the support necessary for properly treating and preventing injury to the sacroiliac joint M. In particular, the brace 10 is configured to overlie the buttocks J and extend downwardly to the crotch O so as to provide an upwardly and forwardly directed compressive force against the sacroiliac joint M when worn. As perhaps best shown in FIG. 5, the back brace 10 selected for illustration generally includes a sacroiliac joint support 12 and adjustable tightening structure 14 for causing the support to exert an upwardly and forwardly directed, adjustable force against the sacroiliac joint M.

Turning initially to the tightening structure 14, the brace 10 includes a flexible wrap 16 (see FIGS. 3 and 6–7) dimensioned to extend around the lower torso E. The wrap 16 comprises a central section 18 and a pair of attachment flaps 20 and 22 projecting from the central section 18 in generally opposite directions. The illustrated flaps 20 and 22 each have a partial oval shape. It will be noted that the central section 18 and the flaps 20 and 22 are formed of separate pieces of material that are attached to one another by suitable means, such as stitching 24 and 26 (see FIG. 6), although a single piece of material may be used to form all three sections of the wrap 16. A reinforcing strip 28 and 30 (see FIG. 7) is connected between the central section 18 and each flap 20 and 22, respectively, by stitching 32 and 34 (see FIG. 6). The reinforcing strips 28 and 30 serve to reinforce the stitching attachment between the central section 18 and the flaps 20 and 22. The flexible wrap 10 further includes structure for adjustably attaching the flaps 20 and 22 to one another along the front side of the body. In particular, the illustrated flaps 20 and 22 include complemental patches 36 and 38 of hook-and-loop fastening material adjacent the rounded ends thereof. This arrangement permits the user to place the central section 18 on the lower back, pull the flaps 20 and 22 about the lower abdomen, and then snugly secure the wrap 16 about the lower torso E. In addition, the adjustability of the fastening structure 36,38 accommodates various body sizes and permits the user to vary the tightness of the brace 10 about the body.

The preferred wrap 16 is formed of an elasticized material having sufficient resiliency to apply compression to the lower torso E when the wrap is tightened about the body. The preferred material comprises a laminate of a foam-type fabric and neoprene, although other suitable materials (e.g., neoprene alone, cloth, elastic mesh, etc.) may be used. It will also be noted that the central section 18 and flaps 20,22 may be formed of dissimilar materials, if desired.

It will particularly be noted that the wrap 16 overlies the lumbar region B of the spine A along the backside of the body. In this respect, the wrap 16 is generally similar to conventional back braces in terms of the location on the body and the general support provided thereby. In other words, the flexible wrap 16 alone is incapable of properly treating and preventing most lower back injuries. In this respect, the support 12 provides one of the more significant distinctions over conventional braces. That is, the support 12 projects from the flexible wrap 16 to overlie the buttocks J and extend downwardly to the crotch O when the brace 10 is donned (e.g., see FIG. 5). The support 12 is consequently operable to exert an upwardly and forwardly directed force against the sacroiliac joint M so as to provide the support necessary for properly treating and preventing most lower back disorders. No back brace has heretofore been capable of providing such support.

In comparing FIGS. 1 and 5 or FIGS. 2 and 4, it will be apparent that the support 12 comprises a flexible element extending from the lumbar region B of the spine A downwardly below the ischial tuberosity K and L of each of the pelvic bones H and I. It will also be noted that because the lowermost connection for the ligaments G is the ischial tuberosities K and L, the support 12 is designed to extend at least to these anatomical landmarks of the body. In fact, the preferred support 12 extends downwardly below the ischial tuberosities K and L to ensure that an upwardly directed force is applied against even the lowermost ligaments of the sacroiliac joint M. The support 12 is consequently dimensioned to overlie the ligaments G of the sacroiliac joint M, which permits the support 12 to exert a compressive force against virtually the entire sacroiliac joint M.

Figure 6:
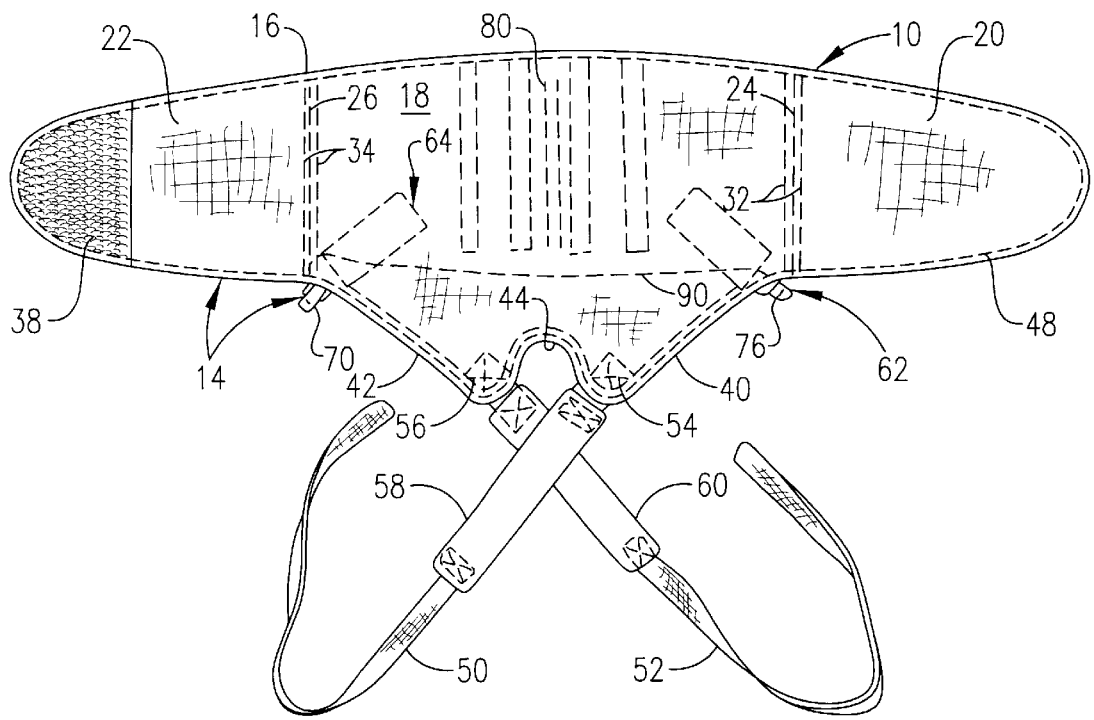
FIG. 6 is an elevational view of the interior side of the back brace removed from the wearer.
Figure 7:
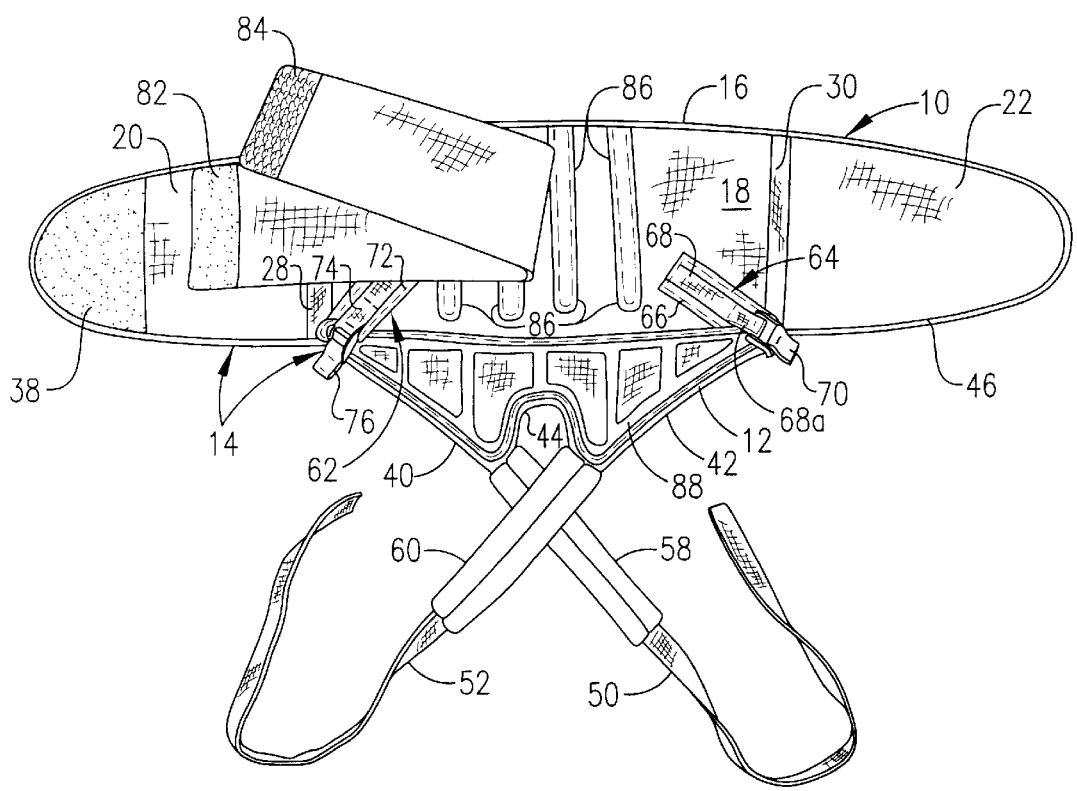
FIG. 7 is an elevational view of the back brace similar to FIG. 6, but illustrating the exterior side of the brace.

The preferred support 12 is formed of the same piece of material forming the central section 18 of the flexible wrap 16 (see FIG. 6). However, it is entirely within the ambit of the present invention to form the support 12 and central section 18 of separate pieces of material and operatively connect the pieces by suitable means, such as laterally spaced apart straps (not shown) stitched between the support 12 and central section 18. In addition, the preferred support 12 includes a second superimposed layer of the material (not shown) to provide additional support. The support 12 presents a pair of lower edges 40 and 42 that converge downwardly from the respective flaps 20 and 22 toward a central, inwardly extending recess 44. In this respect, the support 12 is designed to "cup" the buttocks J (e.g., see FIG. 5), while the recess 44 provides ventilation to the exposed body parts so as to improve the comfort of the brace. It will also be noted that the support 12 does not extend across the front side of the body (see FIG. 3), and accordingly, the brace 10 does not obstruct ventilation to this area of the body. A protective border 46 (see FIG. 7) extending around the support 12 and flexible wrap 16 serves to enhance the appearance of the brace 10, prevent fraying of the edges of the support 12 and wrap 16, and provide additional means for interconnecting the support 12 and wrap 16. As shown in FIG. 6, the border 46 is preferably attached to the support 12 and wrap 16 by stitching 48, although other suitable means may be used.

The tightening structure 14 further includes a pair of relatively non-elastic legs straps 50 and 52 attached adjacent the lower edges 40 and 42 of the support 12 on opposite sides of the recess 44 by suitable means, such as stitching 54 and 56. The straps 50 and 52 are generally aligned with the respective edges 40 and 42 of the support 12 so as to cross over one another when the brace 10 is removed from the body. However, when the brace 10 is worn, the left strap 50 wraps about the left leg P, while the right strap 52 wraps about the right leg Q (see FIG. 3). It is more particularly noted that the straps 50 and 52 each project from the support 12 to pass between the legs P,Q just under the crotch O of the wearer. In this respect, the straps 50 and 52 are preferably each provided with a pad 58 and 60 positioned adjacent the crotch O of the wearer when the brace 10 is worn. The pads 58 and 60 improve the comfort of the brace 10 by distributing the force exerted against the crotch O and the inner thighs of the legs P and Q when the straps 50 and 52 are tightened. In addition, the pads 58 and 60 are preferably formed of a soft, non-abrasive material (e.g., closed cell foam rubber) to prevent chaffing, etc.

A pair of buckle assemblies 62 and 64 are fixed to the flexible element forming the support 12 and the central section 18 of the flexible wrap 16 so as to be positioned along the sides of the wearer when the brace 10 is worn. The buckle assemblies 62 and 64 are associated with a respective one of the leg straps 50 and 52 for adjustably securing the respective strap relative to the support 12. Accordingly, the leg straps 50,52 and buckle assemblies 62,64 are particularly useful in tightening the support 12 against the buttocks J so as to exert a force against the sacroiliac joint G in a generally upward and forward direction. As perhaps best shown in FIG. 7, the right buckle assembly 64 includes a flexible mounting strip 66 stitched to the flexible element forming the support 12 and the central section 18 of the flexible wrap 16. A relatively short, non-elastic strap 68 mounted to the strip 66 presents a loop 68a for attachment to a standard buckle 70. In the usual manner, the buckle 70 releasably couples with the right leg strap 52 to selectively prevent relative movement therebetween. The left buckle assembly 62 is similar in construction to the right buckle assembly 64. Thus, it is sufficient to explain that the left buckle assembly 62 includes a mounting strip 72 fixed relative to the support 12, a coupling strap 74, and a buckle 76 for releasably coupling with the left leg strap 50.

The tightening structure 14 further includes an elongated, flexible cuff 78 dimensioned to wrap around the lower torso E. The illustrated cuff 78 is attached by stitching 80 (see FIG. 6) to the exterior side of the central section 18 of the wrap 16 at a point spaced generally equally between the flaps 20 and 22. Accordingly, the cuff 78 is designed to overlie the flexible wrap 16 when the brace 10 is worn. Adjacent the opposite ends of the cuff 78 are complemental patches 82 and 84 (see FIG. 7) of hook-and-loop fastening material for permitting the user to adjustably tighten the cuff 78 about the lower torso E. Similar to the flexible wrap 16, the cuff 78 is formed of an elasticized fabric so as to provide a compressive force against the lumber region B of the spine A. It is not necessary that the brace 10 include the cuff 78, however, the cuff 78 enhances the support provided by the brace 10 and assists the flexible wrap 16 in tightening the support 12 against the body.

A plurality of elongated, spaced apart cloth strips 86 are stitched to the flexible element forming the support 12 and the central section 18 of the flexible wrap 16 to define an equal number of pockets. The cloth strips 86 extend from the top of the central section 18 downwardly into the support 12 so as to overlie the lumbosacral region B,D of the spine A in a generally vertical orientation when the brace 10 is worn. A stay (not shown) is contained within each of the pockets for providing additional support to this region of the spine. The stays may be formed of various materials depending upon the desired support to be provided thereby. For example, if the stays are designed only to slightly enhance the support provided by the brace 10, the may be formed of a flexible foam material. On the other hand, when the stays are intended to significantly enhance the support provided by the brace 10, the stays may be formed of a relatively inflexible plastic material. In the illustrated embodiment, the pockets are permanently closed by the cloth strips 86, although it is entirely within the ambit of the present invention to leave one end of the cloth strips 86 detached so as to facilitate changing or replacement of the stays, if desired.

In the illustrated embodiment, the brace 10 also includes a reinforcing member 88 comprising a flexible element attached to the exterior side of the support 12 for enhancing the support provided to the sacroiliac joint M. The reinforcing member 88 is generally coextensive with the support 12 below the flaps 20,22 of the wrap 16, with the lower boundary of the member extending along the edges 40,42 and the recess 44 of the support and the upper boundary of the member extending generally linearly between the lower margins of the flaps 20,22. The member 88 is preferably attached to the support 12 by suitable means, such as stitching 90 extending about the perimeter of the member 88 (see FIG. 6). Similar to the support 12, the reinforcing member 88 is preferably formed of an elasticized material, such as neoprene. Moreover, the reinforcing member 88 includes a plurality of stays 92 fixed to the material element at spaced apart locations so as to avoid interference with the overall flexibility of the member 88 and support 12. It will be noted that there are two similar sets of stays, with each set comprising three uniquely shaped stays. The preferred stays 92 are formed of a flexible foam material (e.g., closed cell foam rubber), although other materials may be used to vary the support provided thereby, as noted above. The reinforcing member 88 further includes a protective border 94 stitched around its perimeter to serve generally the same purposes as those noted above with respect to the border 46.

In use, the brace 10 is donned by first positioning the support 12 and the central section 18 of the flexible wrap 16 along the backside of the wearer in generally the illustrated location. The flexible wrap 16 is then tightly secured about the lower torso E by interconnecting the complemental fastening patches 36 and 38 on the flaps 20 and 22, followed by similarly securing the cuff 78 tightly about the lower torso E. The leg straps 50 and 52 are subsequently pulled under the crotch O and around the legs P and Q, and then pulled taut before being coupled with the respective buckles 70 and 76. At this point, the support 12 sufficiently overlies the lumbosacral region B,D of the spine A, the ligaments G, and the pelvic bones H,I to provide the support necessary for treating and preventing injuries to the sacroiliac joint M. Moreover, the adjustability of the flexible wrap 16, the leg straps 50,52 and the cuff 78 allow the brace 10 to accommodate various body sizes and permit the wearer to adjust the compressive force exerted against the sacroiliac joint M by the support 12.

The preferred forms of the invention described above are to be used as illustration only, and should not be utilized in a limiting sense in interpreting the scope of the present invention. Obvious modifications to the exemplary embodiments, as hereinabove set forth, could be readily made by those skilled in the art without departing from the spirit of the present invention. For example, the construction of the tightening structure 14 may be varied if desired.

The inventor hereby states his intent to rely on the Doctrine of Equivalents to determine and assess the reasonably fair scope of the present invention as pertains to any apparatus not materially departing from but outside the literal scope of the invention as set forth in the following claims.

What is claimed is:

1. A device for supporting the sacroiliac joint, said device comprising:

a flexible support dimensioned to overlie the sacroiliac joint along the backside of a user such that the support extends generally from the lumbar region of the spine to at least the ischial tuberosities of the user when the support is tightened against the body, said support being formed of a material that permits generally unrestricted flexing thereof so that the support is configured to generally conform to the shape of the underlying portion of the body when the support is tightened against the body; and an adjustable tightener operatively connected to the support for causing the support to generally conform to the shape of the underlying portion of the body and exert an adjustable force against the sacroiliac joint in a generally upward and forward direction, said tightener including a pair of leg straps projecting from the support and being configured for passage adjacent the user's crotch, said tightener further including a pair of strap connectors spaced above the crotch when the support is tightened against the body and associated with respective ones of the leg straps to permit selective tightening of the straps and consequent tightening of the support into sacroiliac joint-supporting engagement with the body, whereby the support exerts an upwardly and forwardly directed force against the sacroiliac joint when the leg straps are tightened.

2. A device as claimed in claim 1, said support being dimensioned to extend from the lumbar region of the spine downwardly at least to the ischial tuberosity of each of the pelvic bones of the user.

3. A device as claimed in claim 2, said tightener including at least one adjustable band operatively connected to the support and dimensioned to wrap around the body for adjustably tightening the support against the body.

4. A device as claimed in claim 2, said tightener including a flexible wrap dimensioned to extend around the lower torso, said support projecting from the wrap.

5. A device as claimed in claim 4, said wrap including a pair of flaps and fastening structure adjustably fastening the flaps to one another for permitting the user to adjustably tighten the wrap about the lower torso.

6. A device as claimed in claim 5, said fastening structure comprising hook-and-loop fastening material.

7. A device as claimed in claim 4, said wrap and said support being formed of a common flexible element.

8. A device as claimed in claim 7, said flexible element comprising an elasticized material.

9. A device as claimed in claim 4, said tightener including a flexible tightening cuff attached to the wrap and dimensioned to wrap around the lower torso of the user.

10. A device as claimed in claim 9,
said cuff overlying the wrap and including a pair of opposite ends having adjustable attachment structure for adjustably attaching the ends to one another.

11. A device as claimed in claim 1,
said support presenting a pair of lower edges that converge downwardly toward a central, inwardly extending recess that is positioned adjacent the crotch of the user when the support is tightened against the body.

12. A device as claimed in claim 11,
said leg straps projecting from the support adjacent opposite sides of the recess.

13. A device as claimed in claim 1,
each of said connectors comprising a buckle assembly for adjustably securing the respective one of the leg straps relative to the support.

14. A device as claimed in claim 13,
each of said leg straps projecting from the support to underlie the crotch and wrap around the respective leg,
said buckle assemblies being positioned generally on opposite sides of the user when the support is tightened against the body.

15. A device as claimed in claim 14,
each of said leg straps including a pad positioned adjacent the crotch when the support is tightened against the body.

16. A device as claimed in claim 1; and
at least one elongated stay being fixed relative to the support and positioned to overlie the lumbosacral region of the spine in a generally vertical orientation.

17. A back brace comprising:
a flexible wrap dimensioned to extend around the lower torso of a wearer;
a flexible sacroiliac joint support projecting from the flexible wrap to generally overlie the buttocks and extend downwardly to the crotch of the wearer when the brace is worn;
said support being formed of a material that permits generally unrestricted flexing thereof so that the support is configured to generally conform to the shape of the underlying portion of the body when the support is tightened against the body;
a pair of adjustable leg straps operatively connected to the support and being configured for passage adjacent the user's crotch; and
a pair of strap connectors spaced above the crotch when the brace is worn and associated with respective ones of the leg straps for permitting selective tightening of the straps, whereby the support generally conforms to the shape of the buttocks and exerts an adjustable force against the sacroiliac joint in a generally upward and forward direction.

18. A back brace as claimed in claim 17,
said wrap including a pair of flaps and fastening structure adjustably fastening the flaps to one another for permitting the wearer to adjustably tighten the wrap about the lower torso.

19. A back brace as claimed in claim 18,
said wrap being formed of an elasticized material.

20. A back brace as claimed in claim 18,
said fastening structure comprising hook-and-loop fastening material.

21. A back brace as claimed in claim 20,
said support being formed of an elasticized material.

22. A back brace as claimed in claim 17,
said wrap and said support being formed of a common flexible element.

23. A back brace as claimed in claim 22,
said flexible element comprising an elasticized material.

24. A back brace as claimed in claim 17,
said support presenting a pair of lower edges that converge downwardly toward a central, inwardly extending recess that is positioned adjacent the crotch of the wearer when the brace is worn.

25. A back brace as claimed in claim 24,
said leg straps projecting from the support adjacent opposite sides of the recess.

26. A back brace as claimed in claim 17; and
each of said connectors comprising a buckle assembly for adjustably securing the respective one of the leg straps relative to the support.

27. A back brace as claimed in claim 26,
each of said leg straps projecting from the support under the crotch and around the respective leg when the brace is worn,
said buckle assemblies being positioned generally on opposite sides of the wearer when the brace is worn.

28. A back brace as claimed in claim 27,
each of said leg straps including a pad positioned adjacent the crotch when the brace is worn.

29. A back brace as claimed in claim 17; and
a flexible tightening cuff attached to the wrap and dimensioned to wrap around the lower torso of the wearer.

30. A back brace as claimed in claim 29,
said cuff overlying the wrap and including a pair of opposite ends having adjustable attachment structure for adjustably attaching the ends to one another.

31. A back brace as claimed in claim 17; and
at least one elongated stay being fixed relative to the support and positioned in a generally vertical orientation over the lumbosacral region of the spine when the brace is worn.

32. A method for treating and preventing injury to the sacroiliac joint comprising the steps of:
(a) placing a flexible support against the backside of the body to extend generally from the lumbar region of the spine downwardly at least to the ischial tuberosity of each of the pelvic bones of the user; and
(b) tightening the support against the body so that the support conforms generally to the shape of the underlying portion of the body and exerts an upwardly and forwardly directed force against the sacroiliac joint,
step (b) including the steps of wrapping a pair of leg straps projecting from the support under the crotch of the user, adjustable coupling each of the straps to a connector spaced above the crotch, and using the connectors to tighten the straps.

33. A method as claimed in claim 32,
step (b) including the step of placing a flexible wrap operatively connected to the support around the lower torso.

34. A method as claimed in claim 33,
step (b) including the step of adjustably tightening the flexible wrap about the lower torso.

35. A method as claimed in claim 34,
step (b) including the step of tightly wrapping a flexible cuff operatively connected to the flexible wrap around the lower torso.

36. A device for supporting the sacroiliac joint, said device consisting essentially of:
   a support dimensioned to overlie the sacroiliac joint along the backside of a user; and
   an adjustable tightener operatively connected to the support for causing the support to exert an adjustable force against the sacroiliac joint in a generally upward and forward direction,
   said tightener including a wrap dimensioned to extend around the lower torso, with the support depending from the wrap and being configured to extend towards the user's crotch to overlie a portion of the user's buttocks,
   said tightener further including a pair of elongated straps projecting from a lower margin of the support and being configured for passage adjacent the user's crotch and forwardly about a leg of the user, and a connector for each strap located above the lower margin of the support,
   said connectors permitting tightening of the straps and consequent pulling of the support into sacroiliac joint-supporting engagement with the user's buttocks, whereby the support exerts an adjustable force against the sacroiliac joint in a generally upward and forward direction.

* * * * *